United States Patent [19]

Auburn

[11] 4,191,191
[45] Mar. 4, 1980

[54] LAPROSCOPIC TROCAR

[76] Inventor: Robert M. Auburn, 2683 Surfrider Ave., Ventura, Calif. 93003

[21] Appl. No.: 877,270

[22] Filed: Feb. 13, 1978

[51] Int. Cl.² .............................................. A61B 17/34
[52] U.S. Cl. .................................... 128/347; 128/310; 145/616
[58] Field of Search ............... 128/347, 349, 221, 2 B, 128/214.4, 310; 145/61 L, 116 R, 130

[56] References Cited

U.S. PATENT DOCUMENTS

| | | | |
|---|---|---|---|
| 3,630,192 | 12/1971 | Jamshidi | 128/310 X |
| 3,742,958 | 7/1973 | Rundles | 128/347 |
| 3,850,158 | 11/1974 | Elias et al. | 128/2 B |

FOREIGN PATENT DOCUMENTS

| | | | |
|---|---|---|---|
| 1541237 | 7/1969 | Fed. Rep. of Germany | 128/347 |
| 1404851 | 9/1975 | United Kingdom | 145/61 L |

*Primary Examiner*—Stephen C. Pellegrino
*Attorney, Agent, or Firm*—Jack C. Munro

[57] ABSTRACT

The laproscopic trocar which takes the form of an elongated cannula through which to be inserted an elongated sharp pointed instrument. The tip of the instrument includes screw threads with the rear portion of the instrument including a crank assembly. Rotation of the crank assembly causes gradual penetration of the instrument through a patient's abdominal wall.

3 Claims, 5 Drawing Figures

LAPROSCOPIC TROCAR

BACKGROUND OF THE INVENTION

The field of this invention relates to medical instruments and more particularly to a laproscopic trocar which is in common use to penetrate a patient's abdominal wall with a minimum incision and permit the performing of certain surgical procedures through the cannula of the trocar.

The surgical procedure of a laparoscopy is in common use at the present time. Such a surgical procedure normally employs the use of a trocar which is comprised of a cannula or sleeve through which is inserted a sharp pointed tool. This tool is to effect penetration of the abdominal wall thereby permitting the cannula to be inserted through the abdominal wall and remain in place and permit any one of several different types of instruments to be inserted through the cannula to perform surgical procedures within the patient's abdomen. Normally this type of procedure is frequently employed upon women to perform any one of numerous surgical procedures upon the female organs.

The primary advantage to a laparoscopy is that only a small incision is required and a wide range of surgical procedures can be completed through the use of a laproscopic trocar.

However, there are certain disadvantages to the conventional type of laproscopic trocar. The primary disadvantage is that a initial force is usually required in the inserting of the trocar. At times a significant force is required to achieve initial penetration through the abdominal wall and once initial penetration has been obtained, the trocar is easily insertable. As a result the physician is strenuously forcing to obtain insertion of the trocar and after initial insertion the trocar penetrates deeply into the persons abdomen. It is not at all unusual that this deep penetration results in an unnecessary injury within the patient's abdomen. Common types of such injuries are aortic and iliac artery lasceration. Also injuries to the internal organs are common.

SUMMARY OF THE INVENTION

The subject of this invention comprises a modification of a conventional laproscopic trocar structure wherein an elongated sharp pointed penetrating instrument is to be inserted through the elongated hollow cannula of the trocar. The instrument is to be telescopingly movable within the cannula. The sharp pointed end of the instrument includes a series of screw threads with the inner end of the instrument including a crank assembly. The sharp pointed end of the instrument, after being placed within the cannula, is to be placed into physical contact with the patient's abdominal wall. A slight pressure is to be applied against the instrument forcing such into snug contact with the abdominal wall. Subsequent rotation of the instrument causes the sharp point of the instrument to penetrate the abdominal wall with the screw threads permitting gradual entry of the instrument into the peritoneal cavity. The instrument is then withdrawn leaving in place the cannula. Various types of surgical and observation type instruments are to be insertable through the cannula permitting various types of surgical operations to be performed within the patient's abdomen.

The primary objective of this invention is to construct a laproscopic trocar which is to be gradually inserted through the abdominal wall thereby eliminating the potential hazard in the employment of a conventional laproscopic trocar.

A further objective of this invention is to modify the penetration instrument of the laproscopic trocar and to permit the penetrating instrument to be used on existing trocar equipment thereby not requiring the altering of substantial trocar structure.

DETAILED DESCRIPTION OF THE SHOWN EMBODIMENT

Figure 1:
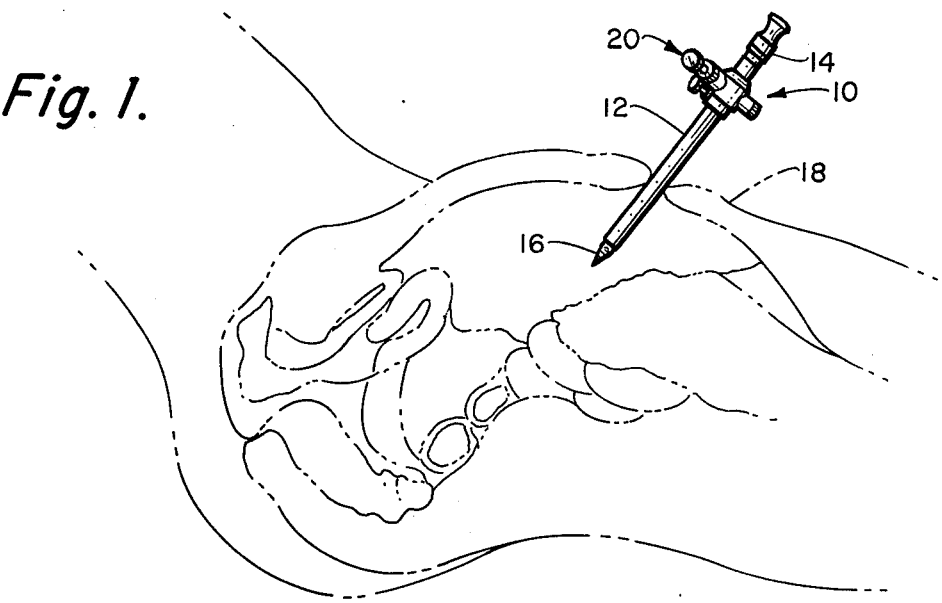
FIG. 1 is an illustrative view showing the insertion of a prior type of laproscopic trocar through the abdominal wall of a patient.

Referring particularly to FIG. 1 there is illustratedly depicted the use of a prior art type of laproscopic trocar 10. The trocar 10 includes the use of a cannula or sleeve 12 within which is telescopingly received a sharp pointed instrument 14. The instrument 14 at the inner end thereof includes an enlarged section to facilitate manual grasping of the instrument 14. The outer end of the instrument 14 is sharp pointed to include a knife edge 16 to facilitate penetration through the abdominal wall 18 of the patient. The instrument 10 includes appropriate valving assembly 20 for the entry and release of gas within the peritoneal cavity. The construction of the valving assembly 20 is deemed to be conventional and forms no specific part of this invention.

Referring particularly to FIGS. 2-5 there is shown the trocar 22 of this invention which is basically similar in construction to trocar 10 in that the cannula 24 is identical as well as the valve assembly 26. However, the sharp pointed instrument 28 not only includes a sharp pointed outer end 30 but also includes a series of helical ridges forming a screw thread arrangement 32.

Fixedly secured to the inner end of the instrument 28 is a crank wheel 34. Attached to the crank wheel 34 adjacent the periphery thereof there is a pin 36. A handle 38 is rotatably mounted on the pin 36.

Figure 2:
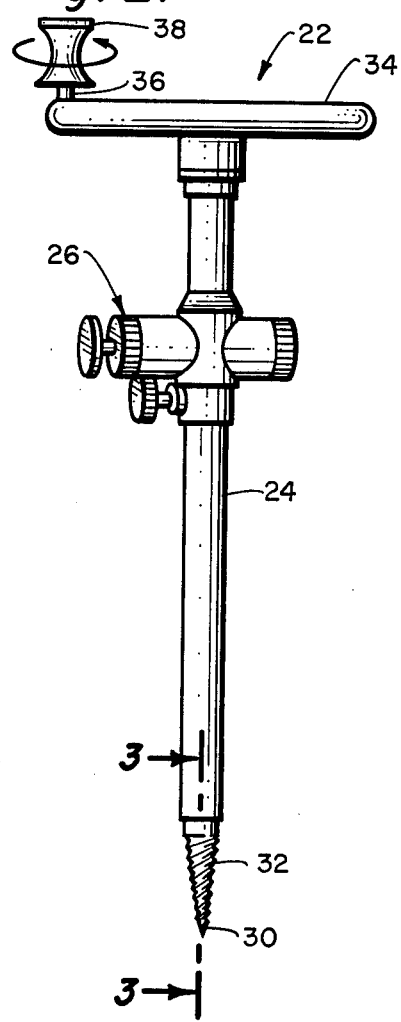
FIG. 2 is a side elevational view of the laproscopic trocar of this invention.

To operate the laproscopic trocar 22 of this invention the physician fully inserts the sharp pointed instrument 28 within the cannula 24 to the position shown in FIG. 2 of the drawing. The physician then places the point 30 against the patient's abdominal wall 18 and exerts a slight pressure against the wall 18 with the result that the point 30 makes an initial incision within the abdominal wall 18. The physician then holds fixed the cannula 24 and grasps the handle 38. The physician then rotates the wheel 34 which in turn causes rotation of the instrument 28. This rotation of the instrument 28 as well as the slight pressure toward the abdominal wall 18 produces a gradual cutting through the abdominal wall 18. This cutting action is facilitated through the use of the screw threading assembly 32.

Upon the tip of the instrument 28 having completely penetrated the abdominal wall 18 and being located within the peritoneal cavity, the forwardmost portion of the cannula 24 also extends within the cavity. The physician then removes the instrument 28 leaving the cannula 24 in position and therefore the cannula 24 is ready to have conducted therethrough other instruments to perform surgical operations within the peritoneal cavity.

Figure 5:
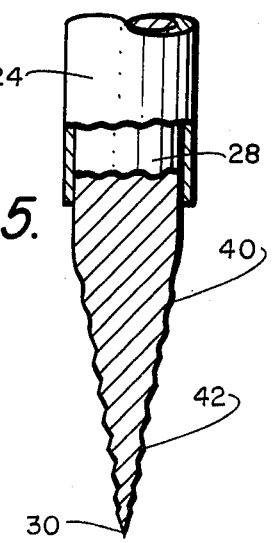
FIG. 5 is a view similar to FIG. 3 but of a modified form of the tip of the penetrating instrument.

Reference is to be had to FIG. 5 wherein a modified form of tip 40 is shown of the instrument 28. The modification regarding the tip 40 relates to the having the screw threaded assembly 42 having a series of sharp pointed helical ridges adjacent the very tip 30 and then a series of smoothly contoured helical ridges spaced from the sharp point 30.

Figure 3:
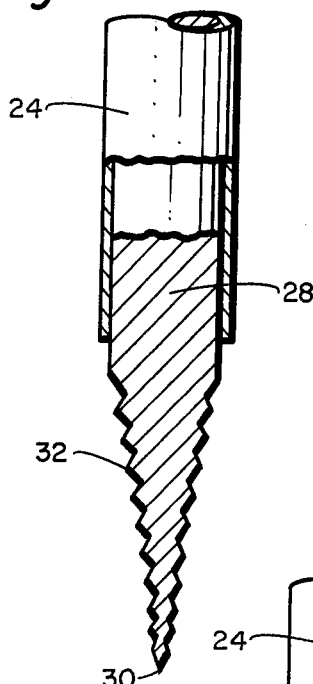
FIG. 3 is an enlarged, partial cross-sectional view of the tip portion of the laproscopic trocar of this invention taken along line 3—3 of FIG. 2.
Figure 4:
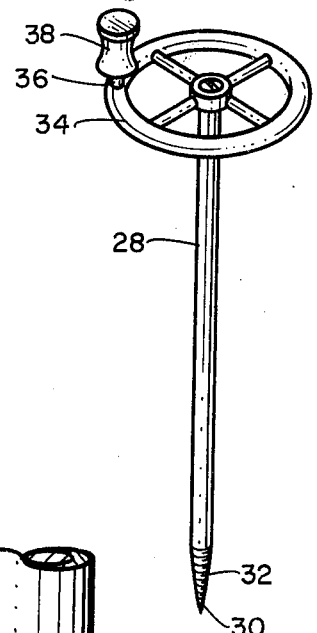
FIG. 4 is a isometric view of the penetrating instrument of this invention employed in conjunction with the laproscopic trocar of this invention.

Within the embodiment shown in FIG. 3 the helical ridges 32 are all sharply pointed. It may be desirable to interpose alternatingly with the sharp pointed ridges a series of smoothly contoured ridges to minimize the tearing of the tissue as the instrument 28 penetrates the abdominal wall 18. It is also considered to be within the scope of this invention that all of the helical ridges 42 be smoothly contoured rather than just some of the ridges 42.

What is claimed is:

1. A laproscopic trocar comprising:
    an elongated cannula having an internal chamber, said cannula having a first opening providing access into said internal chamber and a second opening providing exit from said internal chamber;
    an elongated instrument capable of being conducted through said first opening and into said internal chamber and through said second opening, the outer end of said instrument extending exteriorly of said second opening being sharp pointed, said outer end including a helical ridge, said helical ridge taking the form of a plurality of helical ridges forming a screw thread assembly, whereby said instrument to be inserted within said cannula with said sharp pointed outer end to make initial penetration through a patient's abdominal wall and subsequent rotation of said instrument causes gradual entry of said instrument into the patient's abdomen due to the threading of said helical ridge through the patient's abdominal wall, said screw thread assembly comprises a series of sharp pointed helical ridges and a series of smoothly contoured helical ridges, said sharp pointed helical ridges being located adjacent said sharp pointed outer end.

2. The laproscopic trocar as defined in claim 1 wherein:
    the portion of said instrument extending exteriorly of said first opening comprising the inner end, said inner end including crank means to facilitate rotational movement of said instrument.

3. The laproscopic trocar as defined in claim 2 wherein:
    said crank means includes a crank wheel attached to said instrument, a handle means rotatably mounted upon said crank wheel, whereby said handle means is capable of being grasped to freely rotate with respect to said crank wheel during rotational movement of said instrument.

* * * * *